（12） United States Patent
Kheradvar

(10) Patent No.: US 9,968,445 B2
(45) Date of Patent: May 15, 2018

(54) TRANSCATHETER MITRAL VALVE

(71) Applicant: The Regents of the University of California, Oakland, CA (US)

(72) Inventor: Arash Kheradvar, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days. days.

(21) Appl. No.: 14/898,048

(22) PCT Filed: Jun. 13, 2014

(86) PCT No.: PCT/US2014/042347
§ 371 (c)(1),
(2) Date: Dec. 11, 2015

(87) PCT Pub. No.: WO2014/201384
PCT Pub. Date: Dec. 18, 2014

(65) Prior Publication Data
US 2016/0143730 A1    May 26, 2016

Related U.S. Application Data

(63) Continuation-in-part of application No. 14/221,194, filed on Mar. 20, 2014.
(Continued)

(51) Int. Cl.
*A61F 2/24*    (2006.01)
*A61B 90/00*    (2016.01)

(52) U.S. Cl.
CPC .......... *A61F 2/2412* (2013.01); *A61B 90/37* (2016.02); *A61F 2/2418* (2013.01); *A61B 2090/3782* (2016.02); *A61F 2230/0095* (2013.01)

(58) Field of Classification Search
CPC ........ A61F 2/2412; A61F 2/2418; A61F 2/24; A61F 2/2469; A61F 2/2475;
(Continued)

(56) References Cited

U.S. PATENT DOCUMENTS 3,739,402 A * 6/1973 Cooley ................. A61F 2/2412
                                                    623/2.16
4,259,753 A * 4/1981 Liotta .................. A61F 2/2418
                                                    623/2.18
(Continued)

FOREIGN PATENT DOCUMENTS

WO    WO2013022798    2/2013
WO    WO2013155474    10/2013

OTHER PUBLICATIONS

Gupta et al, Dimensions of the human adult mitral valve in the embalmed cadaver, (Mar. 2013), J. Morphol. Sci., vol. 30, No. 1, pp. 6-10.*
(Continued)

*Primary Examiner* — Paul Prebilic
(74) *Attorney, Agent, or Firm* — Tope-McKay & Associates

(57) ABSTRACT

Described is a transcatheter mitral valve. The mitral valve includes a saddle-shaped annulus frame with two prongs extending therefrom. Two leaflets are attached with the frame and prongs to form a bi-leaflet mitral valve. The frame is collapsible to a collapsed configuration that allows for delivery and implantation at a mitral position. When at the mitral position, the mitral valve expands into an open configuration and is secured in place by a fixture, such as clamps that extend from the frame.

13 Claims, 8 Drawing Sheets

Related U.S. Application Data

(60) Provisional application No. 61/835,083, filed on Jun. 14, 2013.

(58) Field of Classification Search
CPC . A61F 2210/0014–2210/0019; A61F 2220/00; A61F 2220/0008; A61F 2230/0095; A61F 2250/0006; A61F 2250/001
See application file for complete search history.

(56) References Cited

U.S. PATENT DOCUMENTS

| | | | |
|---|---|---|---|
| 5,163,953 A * | 11/1992 | Vince | A61F 2/2418 623/2.11 |
| 6,309,379 B1 | 10/2001 | Willard | |
| 9,572,662 B2 * | 2/2017 | Morriss | A61F 2/2418 |
| 9,839,515 B2 * | 12/2017 | Von Segesser | A61F 2/2436 |
| 2001/0007956 A1 * | 7/2001 | Letac | A61F 2/2412 623/2.11 |
| 2001/0039450 A1 * | 11/2001 | Pavcnik | A61F 2/01 623/1.24 |
| 2005/0101988 A1 | 5/2005 | Stanford et al. | |
| 2005/0154442 A1 | 7/2005 | Eidenschink et al. | |
| 2007/0016289 A1 * | 1/2007 | Johnson | A61F 2/2409 623/2.17 |
| 2007/0043431 A1 * | 2/2007 | Melsheimer | A61F 2/2418 623/1.24 |
| 2007/0100432 A1 * | 5/2007 | Case | A61F 2/2418 623/1.15 |
| 2007/0239254 A1 | 10/2007 | Chia | |
| 2007/0293935 A1 | 12/2007 | Olsen et al. | |
| 2007/0299499 A1 | 12/2007 | Hartley et al. | |
| 2008/0039863 A1 | 2/2008 | Keegan et al. | |
| 2009/0030497 A1 | 1/2009 | Metcalf et al. | |
| 2009/0030512 A1 * | 1/2009 | Thielen | A61F 2/2418 623/2.14 |
| 2009/0099640 A1 | 4/2009 | Weng | |
| 2009/0164003 A1 * | 6/2009 | Kheradvar | A61F 2/2412 623/2.1 |
| 2009/0192585 A1 | 7/2009 | Bloom et al. | |
| 2010/0217382 A1 | 8/2010 | Chau et al. | |
| 2011/0004299 A1 * | 1/2011 | Navia | A61F 2/2418 623/2.18 |
| 2011/0040374 A1 | 2/2011 | Goetz et al. | |
| 2011/0112622 A1 | 5/2011 | Phan et al. | |
| 2011/0196472 A1 | 8/2011 | Sugimoto et al. | |
| 2011/0251664 A1 | 10/2011 | Acosta De Acevedo | |
| 2011/0319988 A1 * | 12/2011 | Schankereli | A61F 2/2418 623/2.11 |
| 2012/0078353 A1 * | 3/2012 | Quadri | A61F 2/2418 623/2.11 |
| 2012/0165916 A1 | 6/2012 | Jordan | |
| 2014/0046433 A1 * | 2/2014 | Kovalsky | A61F 2/2418 623/1.26 |
| 2017/0049565 A1 * | 2/2017 | Bailey | A61F 2/2418 |

OTHER PUBLICATIONS

International Search Report and the Written Opinion of the International Searching Authority for PCT/US2014/042347; dated Nov. 3, 2014.
International Preliminary Report on Patentability for PCT/US2014/042347; dated Dec. 23, 2015.
Office Action 1 for U.S. Appl. No. 14/221,194 (non TMA), dated Feb. 4, 2016.
Response to Office Action 1 for U.S. Appl. No. 14/221,194 (non TMA), dated Aug. 2, 2016.
Office Action 2 for U.S. Appl. No. 14/221,194 (non TMA), dated Dec. 30, 2016.

\* cited by examiner

102

TRANSCATHETER MITRAL VALVE

CROSS-REFERENCE TO RELATED APPLICATIONS

The present application is a National Stage Entry of PCT/US2014/042347, filed on Jun. 13, 2014, which is a Continuation-in-Part application of U.S. patent application Ser. No. 14/221,194, entitled, "Percutaneous Heart Valve Delivery Systems," filed on Mar. 20, 2014.

PCT/US2014/042347 also claims the benefit of U.S. Provisional Application No. 61/835,083, filed on Jun. 14, 2013, entitled, "Collapsible Mitral Valve for Percutaneous Delivery and Implantation."

BACKGROUND OF THE INVENTION (1) Field of Invention

The present invention relates to a heart valve system and, more particularly, to a percutaneous mitral valve for delivery and implantation at a mitral position.

(2) Description of Related Art

Valvular heart disease is the third most common cause of cardiovascular disease in the United States. Mitral Regurgitation (MR) is a common valvular disorder, which can be manifested, in acute and chronic forms. Both the acute and chronic forms of MR are the source of a significant amount of cardiovascular morbidity and mortality. Dysfunction in the mitral valve can arise from abnormalities of any part of the mitral valve apparatus, including the leaflets, annulus, chordae tendineae, and papillary muscles. Additional anatomical support for mitral valve function comes from the loft atrial wall and ventricular myocardium adjacent to the papillary muscles. Proper valve function depends on the interaction of all of the anatomic components and a minor dyssynchrony can result in significant valvular dysfunction. With the deranged valvular structure and/or function permitting back/low there is a resultant left ventricular volume overload. Over time and with deterioration of the mitral valve function, this volume overload results in left ventricular dilation and dysfunction. Left ventricular dysfunction in conjunction with MR can lead to pulmonary hypertension, congestive heart failure and ultimately death. Each year in the United States, there are more than 500,000 patients discharged with the diagnosis of MR, and annually in the United States, some 18,000 patients undergo mitral valve surgery. These statistics illustrate the gravity of this problem and the immense cost burden that it creates.

When addressing MR and its etiologies, it must first be identified if the pathologic regurgitation is a result of a primary abnormality of the valve apparatus or secondary to another cardiac disease. When MR is due to a primary abnormality of the valve apparatus, it is referred to as primary MR. The most common causes of primary MR are mitral valve prolapse, rheumatic heart disease and infective endocarditis. Far less common causes of primary MR include trauma and congenital heart disease such as a valve cleft. Secondary MR is most commonly due to ischemic heart disease, left ventricular systolic dysfunction and dilatation (i.e., Functional MR) and least commonly hypertrophic cardiomyopathy. Finally, in the elderly, annular calcification is a cause of MR, however this rarely progresses past moderate and infrequently requires intervention.

Correction of MR within a certain window minimizes the consequences described above. There is a scientifically well-established cause-and-effect relationship between pathologic MR and its deleterious effects on the left ventricle and the patient's life, in the absence of a secondary cause, it is the abnormal valve that makes the heart and thus the patient sick. Definitive therapeutic options for severe MR remain few and the only truly corrective therapies, which require surgical intervention—commonly associated with a median sternotomy—are presently effective. The currently practiced techniques consist of mitral valve repair and replacement. MR is a mechanical problem, thus medical therapy has been shown to be inadequate, and a mechanical intervention (e.g., repair or replacement) is required to improve mortality. Valve competence needs to be restored in order to remove the volume overload and its deleterious consequences. Another controversy within the field of mitral valve repair and replacement is the timing of the intervention.

Currently, decisions are based on as host of factors including symptoms, quantification of left ventricular ejection fraction, age, functional capacity, regurgitant fraction, regurgitant orifice area and regurgitant volume. Imaging and calculation of quantitative measures are performed primarily by Echocardiography. These factors can be subjective and inaccurate. This leads to eligible patients being passed over and perhaps some patients having operations unnecessarily. Finally, a substantial subset of patients is deemed to not be surgical candidates, due to either co-morbid medical illness, age or other factors.

Percutaneous replacement of a heart valve is an incredible development in patient care and one of the great recent breakthroughs in cardiovascular medicine. However, it has been difficult to apply this technology to the mitral valve given its unique anatomical position close to the left ventricular outflow tract. Thus, development of a percutaneous system for mitral valve replacement has not yet been effectively achieved. Development of a percutaneous technology, which has been proven possible in the aortic position would allow for a cure to a very prevalent human disease, while also alleviating a significant amount of suffering associated with both the disease and the current therapeutic options, and finally allowing a more broad range of patients to benefit from the minimally invasive intervention.

The percutaneous approach to valve replacement is a welcome option for many patients due to its sparing of aggressive surgery and reducing the associated comorbidities based on the minimally invasive nature of the procedure. The lure of percutaneous technologies lies in providing cost-effective solutions to heart valve disease, thereby allowing more timely interventions with acceptable efficacy and minimal complications, especially for patients who cannot undergo surgery. These technologies can help avoid open heart surgery in severely ill patients and reduce the number of reoperations in young patients with congenital heart defects.

Nevertheless, there exists numerous challenges in the design and fabrication of a percutanously delivered mitral valve. For example, one challenge is the development of a system that will secure the valve in place and developing a fully functional and durable valve that can be crimped into a catheter. Transcatheter aortic valve implantation takes advantage of the fact that the stenotic aortic valve is heavily calcified. Thus a stented design is ideal as the calcium acts as an anchor for the stem and keeps the valve from migrating. Placing a stented valve in a non-calcified aortic valve would create a much higher risk for valve embolization. The predominant disease process of the mitral valve is mitral regurgitation. This disease is not generally associated with a heavily calcified valve, although that can be the case. Therefore, a fixation apparatus of a percutaneous mitral valve is critical to maintain valve position in the face of physiologic stress. The developed valve should also be robust enough to last as long as commercially available bin-prosthetic valves yet have a low enough profile that can be delivered though a catheter. Again this challenge is one that can be overcome with careful design and utilizing the natural design that evolution has given to the native mitral valve.

With respect to percutaneous delivery, there are not any currently ongoing clinical trials evaluating a percutaneous valve delivery system for the mitral valve diseases. The mitral valve position presents unique challenges for the placement of a transcatheter valve, including, but not limited to inherent anatomic features of the mitral valve (MV) that make fixation and perivalvular seal with currently available devices a challenge, the lack of a calcium bed to fix the valve, and challenges in delivery catheter size due to the increased annulus diameter of the mitral when compared to the aortic valve. Additionally, there is the question as to the configuration of the prosthetic leaflets, as there may be a potential physiologic advantage of the asymmetric vortex bubble and elliptical flow profile that forms through a bi-leaflet valve, compared to the symmetric, round vortex bubble that develops through as tri-leaflet valve. Finally, there is general consensus that the saddle-shape annulus of the mitral valve is a critical component of the left heart complex, it serves a major role in left ventricular function by helping to maintain LV shape, creating efficient valve closure, robust ventricular filling, and chamber contractility. Destruction of the mitral valve apparatus at the tune of mitral valve replacement causes an immediate decrease in chamber contractility and an increase in afterload as the radius term in the Laplace equation increases. It is therefore crucial to maintain some semblance of proper annulus morphology when creating a percutaneous mitral valve, which does not apply to the aortic valve, and thus again illustrates the importance of this valve and delivery system.

Thus, a continuing need exists for a well-designed percutaneous technology for mitral valve replacement that would revolutionize the treatment of valvular heart disease for millions of people.

SUMMARY OF INVENTION

Described is a transcatheter mitral valve. The mitral valve includes a saddle-shaped annulus frame with two prongs extending therefrom. Two leaflets are attached with the frame and prongs to form a bi-leaflet mitral valve.

In another aspect, the frame and prongs are formed of a shape memory material, such as Nitinol.

In yet another aspect, a fixture extends from the frame. The fixture is, for example, one or more clamps.

Further, the frame is configurable between a collapsed configuration and an open configuration, such the collapsed configuration allows the transcatheter mitral valve to be delivered into position against a native mitral valve annulus and upon expanding to the open configuration, the transcatheter mitral valve is secured in place by the fixture.

In yet another aspect, the leaflets are formed of bovine pericardial tissue, leaflet tissue material, and polymeric material, all of any desired width.

Additionally, the prongs have a prong length, with the prong length being between 5 millimeters and 30 millimeters.

In another aspect, the saddle-shaped annulus frame has an annulus rise reflecting curvature of the saddle-shaped annulus frame, the annulus rise being between 2 millimeters and 5 millimeters.

In yet another aspect, the prongs each include a prong axis and extend from the saddle-shaped annulus frame at an intersection, such that a prong angle exists between the prong axis and a vertical axis rising vertically from the intersection, where the prong angle is between 5 degrees and 40 degrees. In another aspect, the prong angle is approximately 20.2 degrees.

Finally, as can be appreciated by one in the art, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1A:
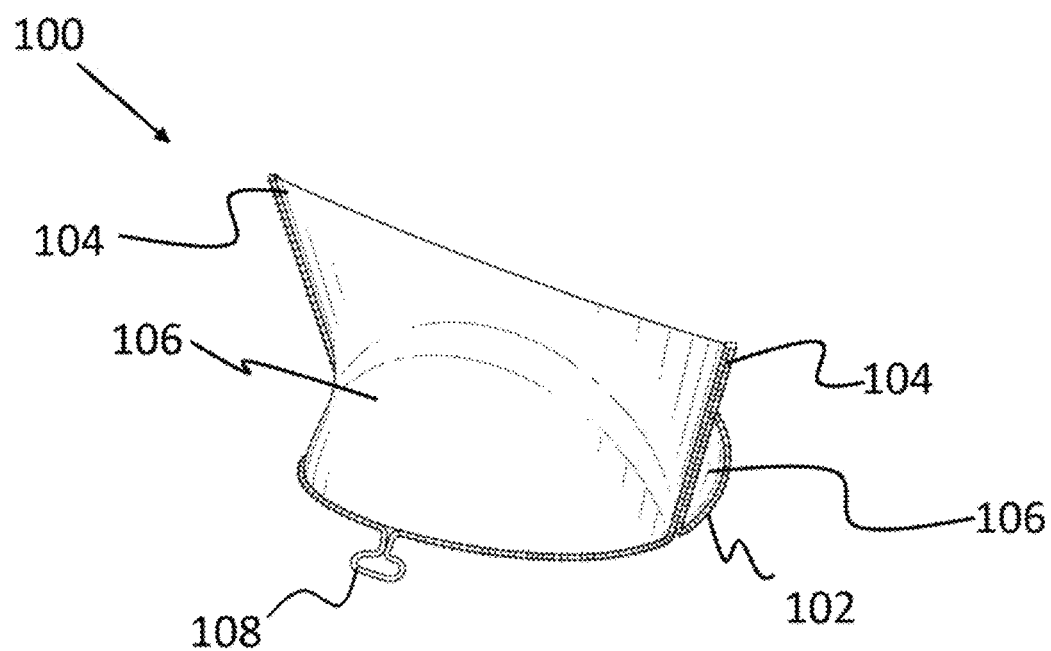
FIG. 1A is an isometric-view illustration of a bioprosthetic mitral valve according to the principles of the present invention.

The present invention relates to a heart valve system and, more particularly, to a percutaneous mitral valve for delivery and implantation at a mitral position. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended, to invoke the provisions of 35 U.S.C. 112, Paragraph 6.

Please note, if used, the labels left, right, rear, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Introduction

A natural mitral valve is a unique valvular structure whose number of leaflets and the saddle shape of its annulus make it distinct from the other three valves inside the heart. To this point, despite an ever growing volume of knowledge existing regarding the unique dynamics of the native mitral valve, a bioprosthesis has not heretofore been developed that capitalizes on these characteristics or employs a bileaflet design. Thus, to fulfill this need, described is a bioprosthetic mitral valve that employs the native saddle shaped annulus and a novel bi-leaflet design. As such, the present invention is directed to a percutaneous bi-leaflet mitral valve and a delivery catheter for transapical implantation of the percutaneous mitral valve. The mitral valve can be implemented and delivered using any suitable delivery system. Thus, also described is a non-limiting example of such a delivery system. Each of these aspects will be described in further detail below.

(2) Specific Aspects

As noted above, described herein is a unique percutaneous bi-leaflet mitral valve. The mitral valve can be formed in any desired shape; however and as shown in FIG. 1A, the mitral valve 100 is desirably formed to replicate the natural design of a mitral valve to provide a physiologic advantage in flow and left ventricular function.

The dynamic motion of the natural or native mitral valve is due to the elastic composition of its fibrous annulus. To imitate the motion of the native mitral annulus, an annular frame 102 is formed that is shaped into a saddle-shaped annulus frame with two prongs 104 extending therefrom for attachment of and holding the leaflets 106 (e.g., bi-leaflets). Thus, the leaflets are affixed with the frame 102 and the prongs 104. The frame 102 is formed of any suitably flexible yet stable material, a non-limiting example of which includes super elastic Nitinol wire. Further, the leaflets 106 are formed of any suitably flexible and biocompatible material, non-limiting examples of which include bovine pericardial tissue, leaflet tissue material, and polymeric material, all of any desired width.

As a non-limiting example, the bovine pericardial tissue is approximately 0.5 mm. Thus, in this example, the frame 102 annulus is sutured to the bovine pericardial tissue leaflets 106.

Further, non-limiting examples of the polymeric material include Polysiloxanes, Polytetrafluoroethylene (PTFE) family, polyurethane, and polyvinyl alcohol (PVA). Polysiloxanes are Silicone and Oxygen based polymers. Other non-limiting examples of polymeric materials include Teflon, ePTFE, Gore-Text®, Dacron based Polyurethanes, including polyester, polyether, polycarbonate, and polysiloxane, J-3 polyurethane (an aliphatic PCU), polyether/PDMS, J-3 polyurethane, Estane (a PEU) and Lycra (a PEUU), and POSS-PCU (polyhedral oligomeric silsesquioxanes-polycarbonate soft segment), a material comprised of interpenetrating networks (IPNs) of Hyaluronan (HA) and Linear Low Density Polyethylene (LLDPE), HA-LLDPE IPNs.

The two leaflets 106 and the saddle-shaped annulus frame 102 are also sutured to each other via the two prongs 104 that extend from the annulus alongside the leaflets 106. The supporting prongs 104 act in similar fashion to the chordae tendineae, preventing the leaflets 106 from being prolapsed toward the atrium.

Figure 1B:
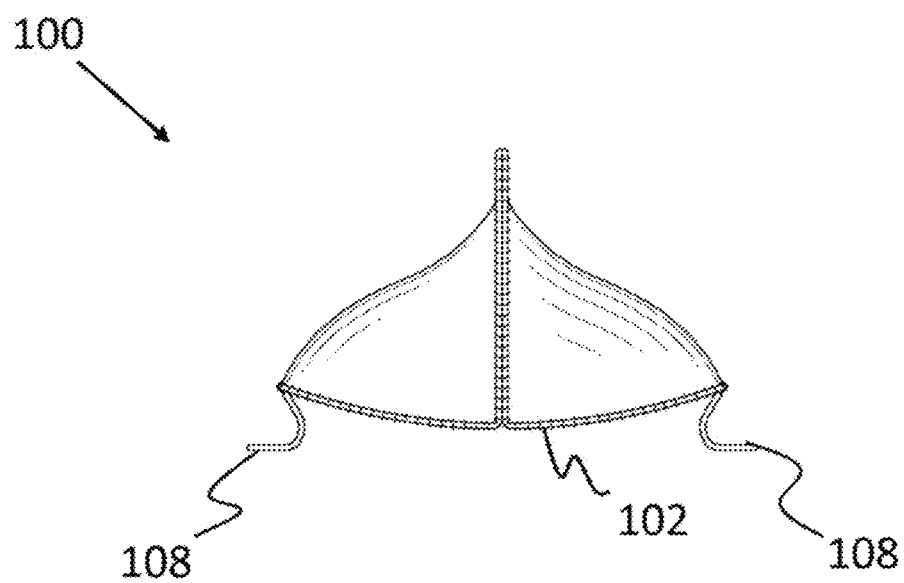
FIG. 1B is a bottom-view illustration of the mitral valve according to the principles of the present invention.
Figure 4A:
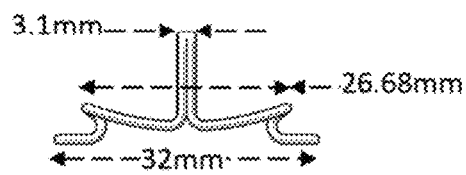
FIG. 4A is a bottom-view illustration of a saddle-shaped annulus frame according to the principles of the present invention.
Figure 4B:
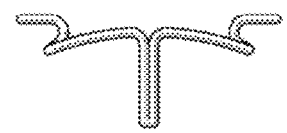
FIG. 4B is an top-view illustration of the saddle-shaped annulus frame according to the principles of the present invention.
Figure 4C:
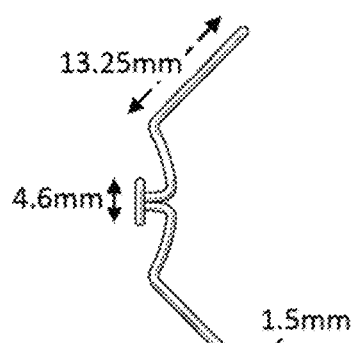
FIG. 4C is a left-view illustration of the saddle-shaped annulus frame according to the principles of the present invention.
Figure 4D:
FIG. 4D is a right-view illustration of the saddle-shaped annulus frame according, to the principles of the present invention.
Figure 4E:
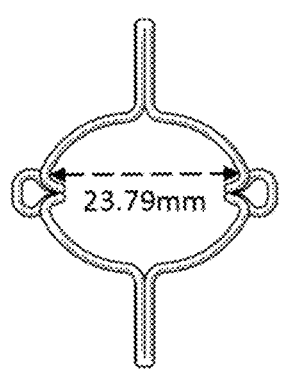
FIG. 4E is a front-view illustration of the saddle-shaped annulus frame according to the principles of the present invention.
Figure 4F:
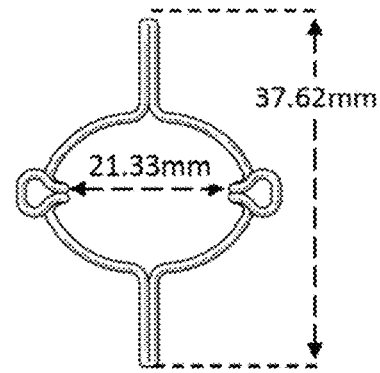
FIG. 4F is a rear-view illustration of the saddle-shaped annulus frame according to the principles of the present invention.
Figure 4G:
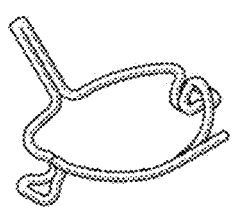
FIG. 4G is an isometric-view illustration of the saddle-shaped annulus frame according to the principles of the present invention.

As will be described in further detail below, the mitral valve 100 can also be formed to include one or more clamps 108 (i.e., a fixture) that extend from the annulus frame 102. As shown in the bottom view of FIG. 1B, the clamps 108 extend from the frame 108 to allow the valve 100 to be compressed for delivery to the implantation site (as shown in FIGS. 4A through 4C) and when implanted, assist in affixing the bioprosthetic mitral valve 100 (of the present invention) with the annulus of the patients existing and natural mitral valve.

Figure 2A:
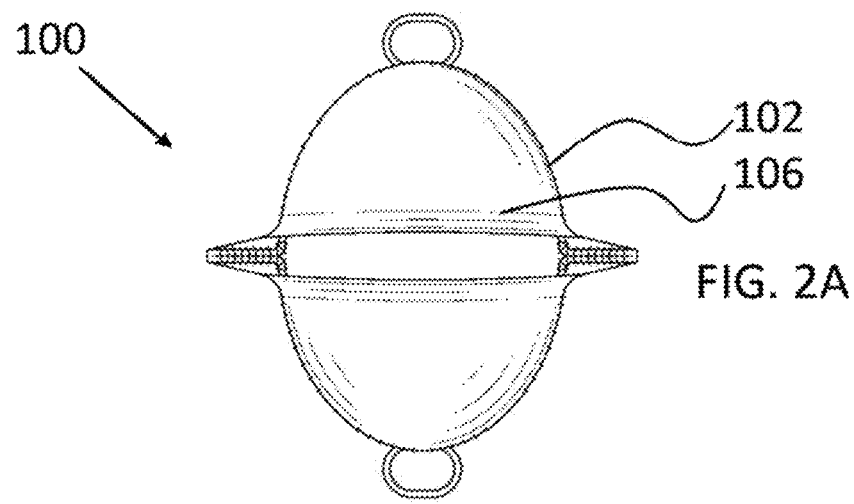
FIG. 2A is a front-view illustration of the mitral valve according to the principles of the present invention, depicting the valve as being open.
Figure 2B:
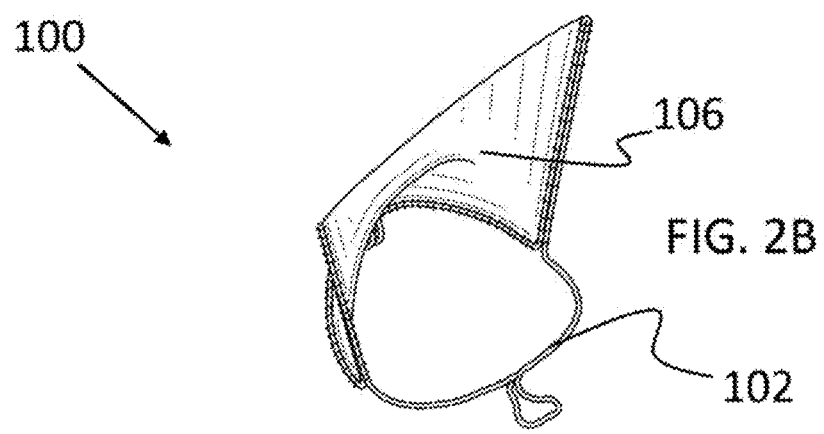
FIG. 2B is an isometric-view illustration of the mitral valve according to the principles of the present invention, depicting the valve with foreground leaflets removed for illustrative purposes.
Figure 2C:
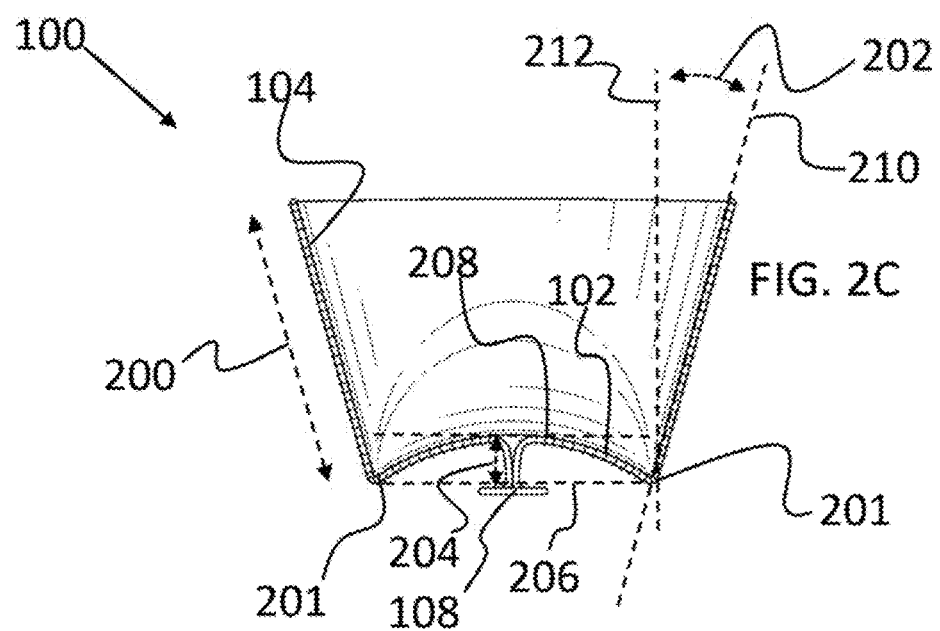
FIG. 2C is a left-view illustration of the mitral valve according to the principles of the present invention, depicting the valve with foreground leaflets removed for illustrative purposes.

For further understanding, FIGS. 2A through 2C depict front, isometric, and left views, respectively, of the mitral valve 100. FIG. 2A illustrates the frame 102 and the bi-leaflet 106 design. It should be understood that the valve 100 can be formed of any suitable dimensions to be positioned within a patient's existing natural mitral valve annulus. As a non-limiting example, the mitral valve 100 can be designed for an adult heart with an annulus frame 102 diameter of between 15 and 35 millimeters. In another aspect, the frame 102 diameter is approximately 25 mm (or a radius of 12.5 mm).

As show in the front view of FIG. 2A, the valve 100 is shown as fully open, with the leaflets 106 in an open position to allow blood or fluids to pass therethrough. For further understanding, FIG. 2B shows an isometric-view, depicting a mid-section of the valve (with a front leaflet removed for illustrative purposes). As shown, the Nitinol annulus frame 102 is surrounded by the pericardial tissue (i.e., leaflet 106 material).

The dynamic nature of mitral annulus motion has been verified previously in humans and in animal models. For example, Carlhäll et al. showed that the excursion of the mitral annulus significantly accounted for the total left ventricular filling and emptying in humans (see Carlhäll C. Wigström L, Heiberg E, Karlsson M, Bolger A, Nylander E. Contribution of mitral annular excursion and shape dynamics to total left ventricular volume change. *American Journal of Physiology-Heart and Circulatory Physiology.* 2004; 287:H1836-H1841). This situation arises mainly because the annulus plays a sphincter-like role when facilitating ventricular filling and valve closure during diastole and systole, respectively. In addition, the geometry of the mitral annulus has been shown to be a significant parameter in the diagnosis of functional disorders such as mitral valve prolapse, functional mitral regurgitation and acute ischemic mitral regurgitation. The mitral valve is a major contributor of the ventricular flow pattern, which is extremely critical with respect to momentum transfer, energy dissipation and the pumping efficiency of the left ventricle. Thus proper design of the Nitinol saddle annulus for the valve is critical to maintaining a novel and bio-inspired approach to create the first bioprosthetic mitral valve that mimics native physiology.

For further understanding, FIG. 2C is a left view of the image shown in FIG. 2B, depicting the valve 100 in an open configuration. Of particular note is the prong length 200, prong angle 202, and annulus rise 204. The prong length 200 is the length of the prong 104 as it rises from an intersection 201 of the frame 102. The prong length 200 is formed at any desired length. Desirably, the prong length 200 is sufficiently long to allow the annulus frame 102 to rest against the annulus of the native mitral valve, while extending from the intersection 201 to a length that allows the leaflet 106 to cover (or support) an existing native mitral valve leaflet. As a non-limiting example, the prong length 200 is between 5 and 30 mm. In another aspect, the prong length 200 is desirably approximately 11 mm or 25 mm. For example, if approximately 11 mm, then the valve 100 would be considered a short leaflet valve. Alternatively, if approximately 25 mm, then the valve 100 would be considered a long leaflet valve.

The annulus rise 204 is a measurement that reflects the curvature of the saddle-shaped annulus frame 102. In other words, the annulus rise 204 is the distance between a line 206 that crosses the bottom most portion of the frame 102 (illustrated at the intersection 201) and a line 208 that crosses an apex of the curvature. The annulus rise 204 is any desired distance that operates to maximize flow and valve 100 function and that assists the valve 100 in maintaining affixation with a native mitral valve. Further, the annulus rise 204 assists in positioning the clamps 108 such that they operate effectively to clamp the valve 100 against the native mitral valve annulus. As a non-limiting example, the annulus rise 204 is between 2 and 5 mm. As another non-limiting example, the annulus rise 204 is approximately 3.25 mm.

The prong angle 202 is the angle between a prong axis 210 and a vertical axis 212 rising vertically from an intersection 201 (i.e., the point at which the prong axis 210 begin). The prong angle 202 is an suitable angle that operates to maximize flow and valve 100 function and that assists the valve 100 in maintaining affixation with a native mitral valve. As a non-limiting example, the prong angel 202 is between 5 and 40 degrees. In another aspect and as another non-limiting example, the prong angle 202 is approximately 20.2 degrees.

The mitral valve 100 has been designed to exhibit optimal fluid dynamics with minimal stress development over the leaflets 106. To understand the effectiveness of a traditional bi-leaflet valve, a study was conducted to examine the effect of a dynamic saddle annulus on transmitral flow and stress distribution among the leaflets.

To begin the analysis of a traditional bi-leaflet valve, the stress distribution over the valve leaflets was computationally modeled. The solid geometry of the Nitinol framework and the leaflets were independently developed and imported into a computational analysis software environment. CATIA (by Dassault Systèmes Americas Corp., located at 175 Wyman Street, Waltham, Mass. 02451, USA) and ABAQUS (by SIMULIA, a division of Dassault Systémes Americas Corp.) were utilized for mechanical design and computational analysis, respectively. Additionally, an in vitro hemodynamic study was undertaken using a heart-pulsed flow duplicator. Transmitral vortex formation was also studied using the same system, for several different sizes of the valve to determine which one replicates the native mitral valve flow the best.

The results of the study were compelling in demonstrating that bi-leaflet valves, regardless of their leaflets' height, produced a more physiologic transmitral vortex and a more favorable stress distribution when compared to the standard tri-leaflet bioprostheses. In normal hearts, the leading vortex of the native asymmetric transmitral vortex transfers extra momentum from the left atrium to the left ventricle, thus contributing to an efficient transport of blood towards the aorta. The additional sources of momentum-transfer derive either from the added mass effect, in which the streamlines act as a boundary that drives the ambient fluid into motion when the vortex is being thrilled, or from fluid entrainment inside the isolated transmitral vortex bubble. The proximity of the leaflet tips to the ventricular wall will significantly affect the process of vortex formation, and the flow pattern observed downstream of the bileaflet prototype that generates an asymmetric vortex may be closer to reality as shown before. Additionally, a major concern with an bioprosthetic heart valve is durability. Minimizing the stress on the leaflets and distributing it more evenly is critical to maintaining functionality and durability of the valve.

Figure 3:
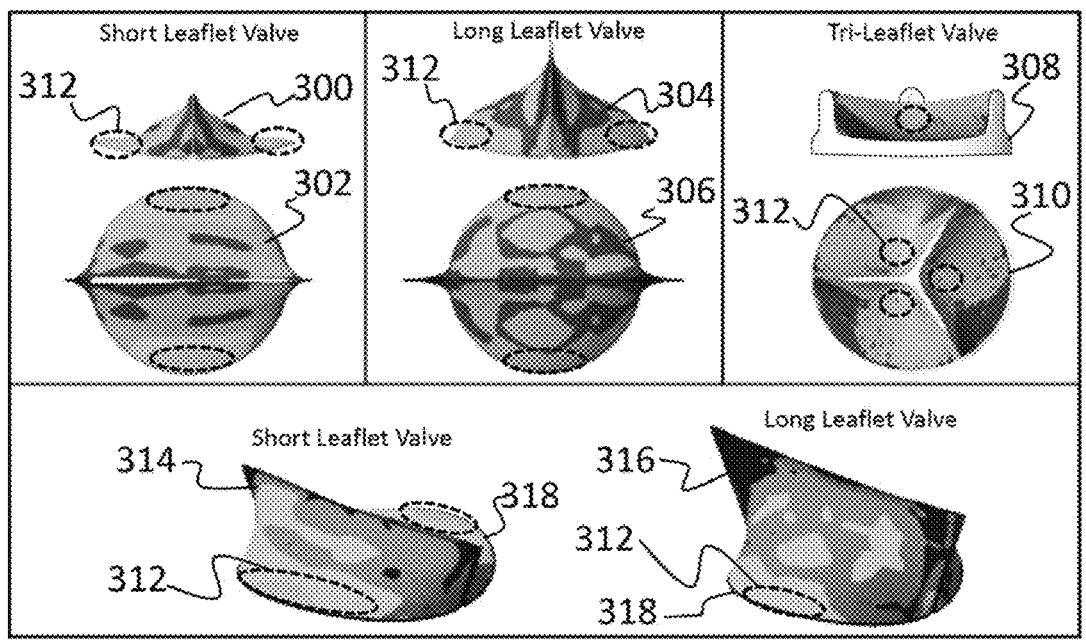
FIG. 3 is an illustration depicting stress test results of a short and long bi-leaflet type valve, as contrasted with a tri-leaflet type valve.

As illustrated in FIG. 3, using a Von Mises stress distribution, it was shown that stress distribution over the leaflets in a bi-leaflet type valve during valve closure was more even and reduced in a bi-leaflet valve with a dynamic annulus when compared to standard tri-leaflet valve with rigid annulus. In a bi-leaflet type valve, more of the stress was transferred to the annulus which improves durability. Specifically, FIG. 3, illustrates testing results of two versions of a bi-leaflet type valve (i.e., short leaflet valve and long leaflet valve). Depicted at the top of FIG. 3 are a bottom view 300 and front view 302 of the stress distribution over the leaflets of a short leaflet bi-leaflet valve. Also depicted are a bottom view 304 and front view 306 of the stress distribution over the leaflets of long leaflet bi-leaflet type valve. The short and long bi-leaflet type valves are to be contrasted with the stress distributions of a traditional tri-leaflet valve, shown in the bottom 308 and front 310 views, respectively. The lighter areas in the images illustrate higher stress regions or points, with the areas of greatest stress 312 for each design being circled with a dashed line. As clearly illustrated in the isometric views of the short leaflet bi-leaflet type valve 314 and long leaflet bi-leaflet type valve 316, higher concentrations of stress is developed over the saddle-shape annulus 318 compared to the leaflets in the bi-leaflet type valves.

Thus, as described above and illustrated, the bi-leaflet design is more favorable with regard to left ventricular hemodynamics and stress on the bioprosthetic leaflets. Given the previous research briefly described above, it affirms advantages of the transcatheter bi-leaflet mitral valve for transapical implantation. To assist in transcatheter delivery, the valve 100 must be collapsible and formed in a catheter based design.

To form the frame 102, a mold can be used that mimics the saddle shape annulus of the native mitral valve. The mold is formed of either aluminum or stainless steel (or any other suitable material) based on the temperature of the furnace that is used for heat treatment, which is determined in conjunction with a machinist skilled in the art, CATIA design software is used for part design, and fabrication of the mold can be easily accomplished using a hired machinist that is skilled in the art, such as those commonly employed by the University of California Irvine, in Irvine, Calif., USA. The mold is used to mount the frame material for heat treatment. As a non-limiting example, the mold is used to mount the Nitinol wires for heat treatment.

Nitinol alloys are materials that have two very unique properties: shape memory and superelasticity. Shape memory refers to the ability of Nitinol to deform at one temperature, and then recover its original, undeformed shape upon heating above its "transformation temperature". Superelasticity occurs at a narrow temperature range just above its transformation temperature; in this case, no heating is necessary to cause the undeformed shape to recover. Nitinol exhibits enormous elasticity, some 10-30 times that of ordinary metal. Thus, Nitinol is used in this design (as a non-limiting example of a suitable frame material) to provide a collapsible frame for the valve. Once the mold is formed to mimic the saddle shape of the native mitral valve annulus, the Nitinol is heat treated in the mold to generate a new resting shape of the valve annulus frame.

Non-limiting examples of a suitable annulus frame 102 are illustrated in FIGS. 4A through 4G, which illustrate a bottom view, a top view, a left view, a right view, a front view, a rear view, and an isometric view, respectively, of the frame 102. It should be noted that the specific dimensions illustrated in FIGS. 4A through 4G are provided for illustrative purposes of a single non-limiting example of suitable dimensions. Importantly, it is to be expressly understood that the present invention is not intended to be limited thereto and that the illustrated dimensions are provided as but one non-limiting example of such suitable dimensions. As noted above, valve characteristics, such as annulus height (i.e., prong length), curvature (i.e., annulus rise) and the critical prong angle, are optimized by constraining the Nitinol wire to a specialized mold designed for an adult heart with an annulus diameter of approximately 25 mm (or any other suitable dimension as described above).

In one aspect, once the Nitinol annulus frame 102 has been formed it will be fused to two Nitinol supporting prongs 104 that extend from the annulus frame 102 alongside the leaflets 106. The supporting prongs 104 can be formed or fused to the frame using any suitable formation or fixation technique, non-limiting examples of which include being wielded to the frame 102, being press fit within a tiny tube, or both, or any other suitable technique.

The supporting prongs 104 act in similar fashion to the chordae tendineae, preventing the leaflets from being prolapsed toward the atrium. All Nitinol components of the valve 100 will share super-elastic properties and thus be amenable to the deformation required to fit into the delivery system. Proper design and optimal spread of these prongs 104 are critical, as the bovine pericardial leaflets 106 will ultimately be sutured to the prongs 104.

A fabric or sheet material can optionally be used to enclose the Nitinol annulus frame 102 and prongs 104. As a non-limiting example, a polyester stretch fabric, which is commercially available from Bard Medical (located at 8195 Industrial Boulevard, Covington, Ga. 30014, USA), can be used to enclose the Nitinol annulus frame 102 and support prongs 104. This fabric serves the purpose of creating a surface which the pericardial leaflets 106 can be sewn to, and providing the annular frame 102 with a surface or substrate that will induce a more rapid overgrowth by the endothelium. The sooner the percutaneously placed valve 100 has its annulus frame 102 covered by endothelium, the more stable the bioprosthesis will be. Finally, the pericardial leaflets 106 will be sutured to the prongs 104 and/or frame 102. Once the leaflets 106 are secure, the mechanical assembly of the valve 100 will be complete and the valve 100 can be implanted within the patient through percutaneous transcatheter delivery. It should be noted that in one aspect, the fabric or sheet is used and attached to the frame 102 and prongs 104. In another aspect, the leaflets 106 are attached directly to the frame 102 and prongs 104 without the inclusion of such a fabric or sheet.

Figures 5A, 5B, 5C:
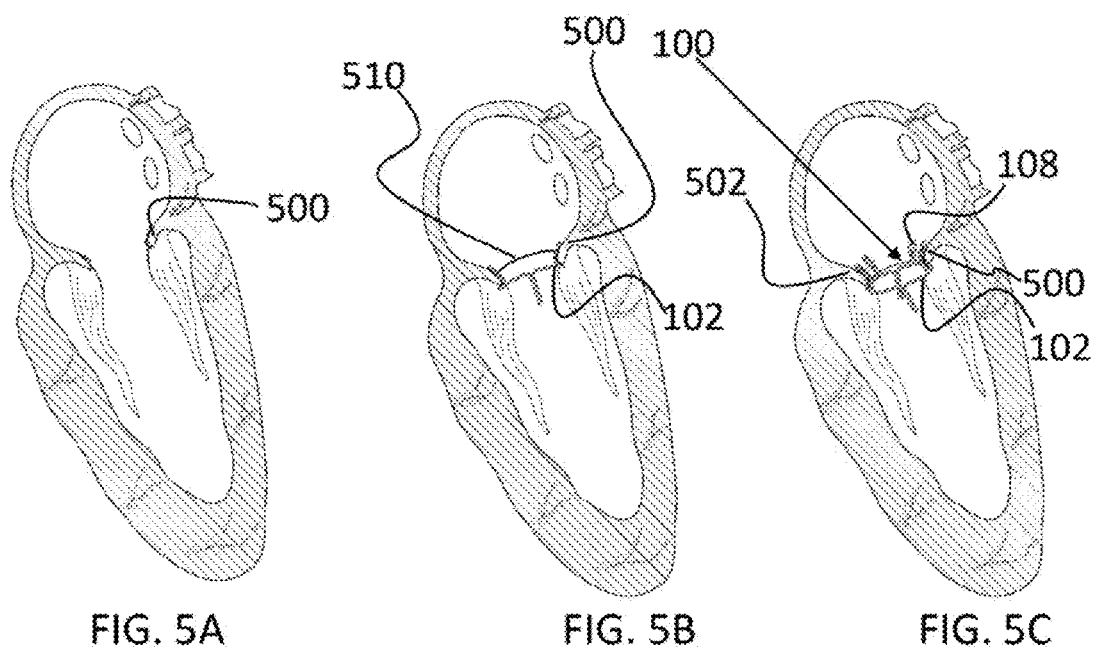
FIG. 5A is an interior-view illustration of a heart chamber, depicting a native mitral valve annulus.
FIG. 5B is an interior-view illustration of the heart chamber, depicting a bioprosthetic mitral valve as attached with a native mitral valve according to the principles of the present invention.
FIG. 5C is an interior-view illustration of the heart chamber, depicting a bioprosthetic mitral valve as attached with a native mitral valve according to the principles of the present invention.

To achieve stability and fixation in the mitral valve annulus, the valve frame 102 can be formed to include a sub-annular fixture. The sub-annular fixture is any suitable mechanism or device that assists the valve 100 in securely attaching to the patient's existing mitral valve annulus. Two non-limiting examples of such a fixture are described below. For example, the annulus frame 102 can machined to include one more Nitinol clamps 108 (e.g., between two to ten; however, desirably, two) that are machined into the frame 102. In this example and as shown in FIG. 5C, the Nitinol clamps 108 will be evenly distributed below the annulus 102. Which upon valve expansion, the Nitinol annulus 102 would be triggered to spring closed and grasp the native valve annulus 500 between the clamp 108 and the Nitinol annulus frame 102. For further understanding, FIG. 5A is an interior view of a heart chamber, depicting a native mitral valve annulus 500. FIG. 5C is an interior view of the heart chamber, showing the Nitinol clamps 108 as extending radially from the annulus frame 102 of the mitral valve 100 to grab the heart tissue 502 and fix the valve 100 in place against the native mitral valve. Note that the valve leaflets are removed for illustrative purposes.

Mother example of a design for the fixture is illustrated in FIG. 5B and includes a second Nitinol annular ring 510, which would sit below the first (i.e., the annular frame 102), allowing the capture of the native annulus 500 between the two rings 510 and 102. In other words, in this aspect, the valve is a dual ring version that includes two rings (i.e., frame 102 and ring 510) that are connected with one another, with one sitting on the atrial side and the other on the ventricular side of the annulus 500 and press the annulus 500 between them. Although not strictly required, in one aspect, it is desirable for the second Nitinol annular ring 510 to be slightly thinner and more collapsed in the delivery catheter than the first ring (i.e., the annular frame 102).

A reduction in collapsed size is critical when designing a percutaneous heart valve, as the smaller the collapsed configuration, the lower profile the delivery system can be, whether that is transapical or transfemoral. The super-elastic properties of Nitinol will allow for the valve to be deformed fitting the design of the catheter. When the profile or French size of the delivery system is minimized, then the myocardial injury, in the case of transapical, or vascular injury in the case of trans-femoral, can be minimized.

Figure 6A:
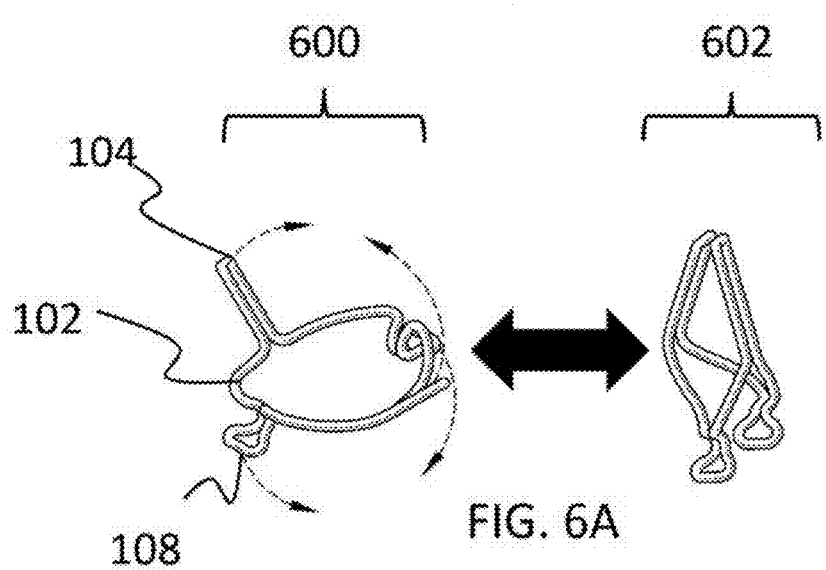
FIG. 6A an isometric-view illustration of the saddle-shaped annulus frame, depicting the frame as changing between an open and collapsed configuration.
Figure 6B:
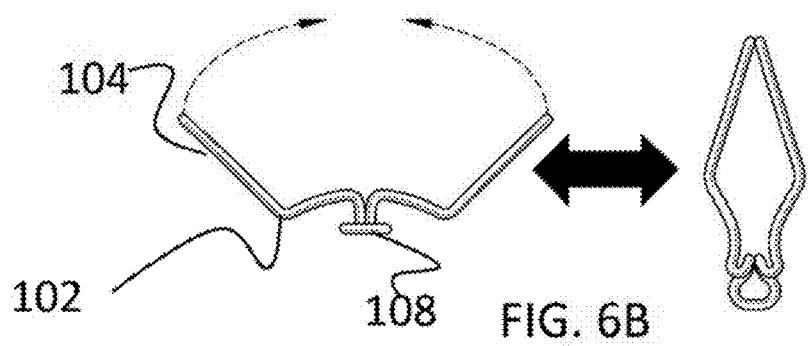
FIG. 6B a side-view illustration of the saddle-shaped annulus frame, depicting the frame as changing between an open and collapsed configuration.
Figure 6C:
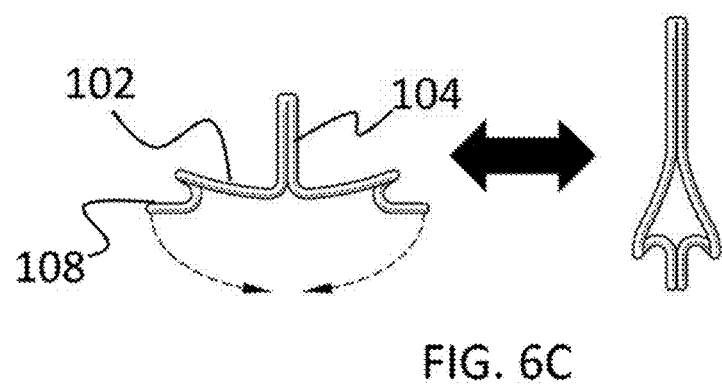
FIG. 6C a front-view illustration of the saddle-shaped annulus frame, depicting the frame as changing between an open and collapsed configuration.

For example, FIGS. 6A, 6B, and 6C illustrate isometric, side, and front views, respectively, of the annular frame 102. Specifically, the figures depict the annular frame 102 as folding between an open configuration 600 and a collapsed configuration 602. Also as shown, the frame 102 is moved into the collapsed configuration 602 by pressing the clamps 108 toward one another and the prongs 104 toward one another. Because the Nitinol annular frame 102 is shape set into the open configuration 600, once delivered to the appropriate place and released, the annular frame 102 will automatically revert from the collapsed 602 to open configuration 600, thereby affixing the valve in place against the native mitral annulus.

Thus, and as mentioned above, the present invention also includes a delivery system that could fascilitate transapical implantation or transfemoral or direct aortic delivery routes to the mitral valve that delivers the mitral valve in the collapsed configuration 602 and once released, allows the mitral valve to revert to the open configuration 600 and become affixed with the native mitral valve. It should be understood that the specific delivery catheter as described and illustrated is provided as a non-limiting example of such a delivery system and that any other suitable mitral valve delivery system can be employed to implant the mitral valve against the native mitral annulus.

For example, the design is for a transapical delivery system to optimize the repositionability of the valve due to the anatomic, position for the mitral valve. The catheter is minimized in size to provide the lowest diameter possible to minimize apical injury on implantation and bleeding risk once the catheter is removed. As a non-limiting example, the catheter has a diameter in range of 12 Fr to 32 Fr.

As noted above, the catheter is directed to the transapical approach. There are several advantages to this approach. To begin with, the anatomical position of the mitral valve makes a transfemoral approach much more complicated than it is for the aortic valve. Accessing the mitral valve from a transfemoral approach requires either a venous approach with a puncture through the intra-atrial septum, or an approach through the aortic valve initially then retrograde through the mitral. Both vascular approaches have major drawbacks and complications. For instance, as with all procedures involving percutaneous vascular access, the risks of bleeding and major vascular injury are significant. Additionally, a transapical catheter allows a larger internal diameter than a transfemoral catheter. With a transapical approach, there is a cardiothoracic surgeon present and the risks of bleeding are less. Additionally there are less common complications such as persistent shunt that occurs after transseptal puncture, left ventricular injury and malignant arrhythmia when taking a retrograde approach. Therefore, due to the advantages discussed above, the catheter is devised for the transapical approach for mitral valve implantation. Goals of the catheter are: (1) A low profile, to enhance access and improve closure (2) Hemostatic control to minimize blood loss during insertion, and (3) Minimal left ventricular trauma during insertion.

Figure 7A:
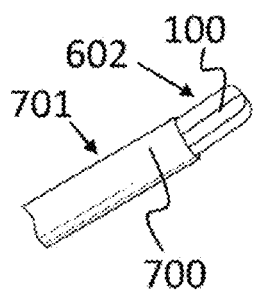
FIG. 7A is an illustration of a delivery catheter according to the principles of the present invention, depicting the mitral valve as starting to protrude from the delivery catheter.
Figure 7B:
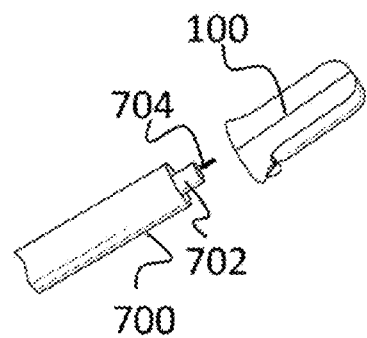
FIG. 7B is an illustration of a delivery catheter according to the principles of the present invention, depicting the mitral valve as removed from the delivery catheter.
Figure 7C:
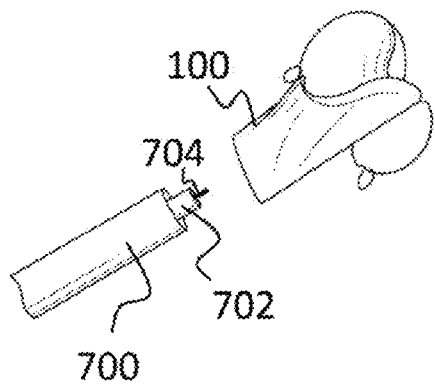
FIG. 7C is an illustration of a delivery catheter according to the principles of the present invention, depicting the mitral valve as expanding from the collapsed to the open configuration.
Figure 7D:
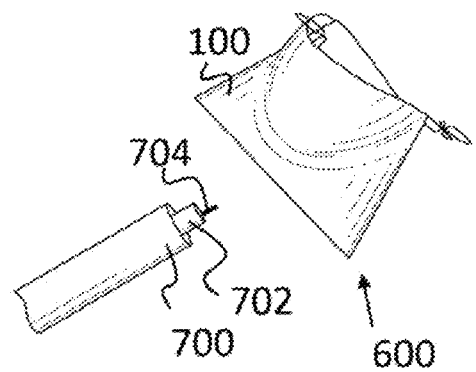
FIG. 7D is an illustration of a delivery catheter according to the principles of the present invention, depicting the mitral valve in the open configuration.

Currently there are several transapical delivery systems for the various transcatheter aortic valves. These systems consist mainly of a main delivery catheter, an external delivery control system and a balloon lumen for those valves that are balloon expandable. As applied to the present mitral valve and as show in FIGS. 7A through 7D, there is no balloon lumen to deal with as using the superelastic properties of Nitinol results in a self-expanding valve 100 that transforms from the collapsed configuration 602 to the open configuration 600 when released from the delivery catheter. Specifically, FIG. 7A illustrates an example schematic of a first stage of transapical valve delivery where the valve 100 is starting to protrude from the delivery catheter 701 (and its sheath 700). FIG. 7B illustrates the still crimped valve 100 once it has been removed from the delivery catheter for positioning, while FIG. 7C illustrates a partially unfolded valve 100. Finally, FIG. 7D illustrates a fully unfolded valve in the open configuration 600. Notably, in FIGS. 7C and 7D, posterior leaflets are removed for illustrative purposes.

As noted above and as shown in FIGS. 7A through 7D, the delivery catheter 701 includes a sheath 700 with a size on the order of 25-30 French (or any other suitable size), which is consistent with the sizing dimensions commercially available today in the United States and Europe. This catheter is designed with a corresponding dilator with a central lumen 702 for a rigid wire 704 that will be inserted to start the delivery process. The catheter 701 and sheath 700 design are well-developed technologies that are clearly understood by those skilled in the art.

In this case, the valve 100 is crimped (into the collapsed configuration 602) and positioned in the sheath 700. When in the desired location, the rigid wire 704 is pushed to force the valve 100 from the sheath 700 to engage with and attach with the native mitral annulus.

It should be noted that in addition to the sheath 700 design, the catheter 701 includes an external delivery and control system (i.e., handle). This system will consist of a one handed control that will allow the operator four degrees-of-freedom, with movement in the x, v and z planes, along with rotation along the axis of the sheath 700. Once the valve 100 is in optimal position, the device will allow the operator to partially deploy the valve to ensure optimal position under Fluoroscopy and 3-Dimensional Transesophageal Echocardiography. Such a catheter and delivery and control system is described in U.S. patent application Ser. No. 14/221,194, entitled, "Percutaneous Heart Valve Delivery Systems," filed on Mar. 20, 2014, which is hereby incorporated by reference as though fully set forth herein.

Based on this concept, if the valve is not in optimal position, the delivery and control system will allow for re-sheathing of the valve 100 and the ability to re-deploy in an alternate location. After an optimal position has been obtained, the system will release the valve and it will secure itself in place. Another advantage to the transapical system is the decreased complexity in movement of the delivery and control system.

Figure 8:
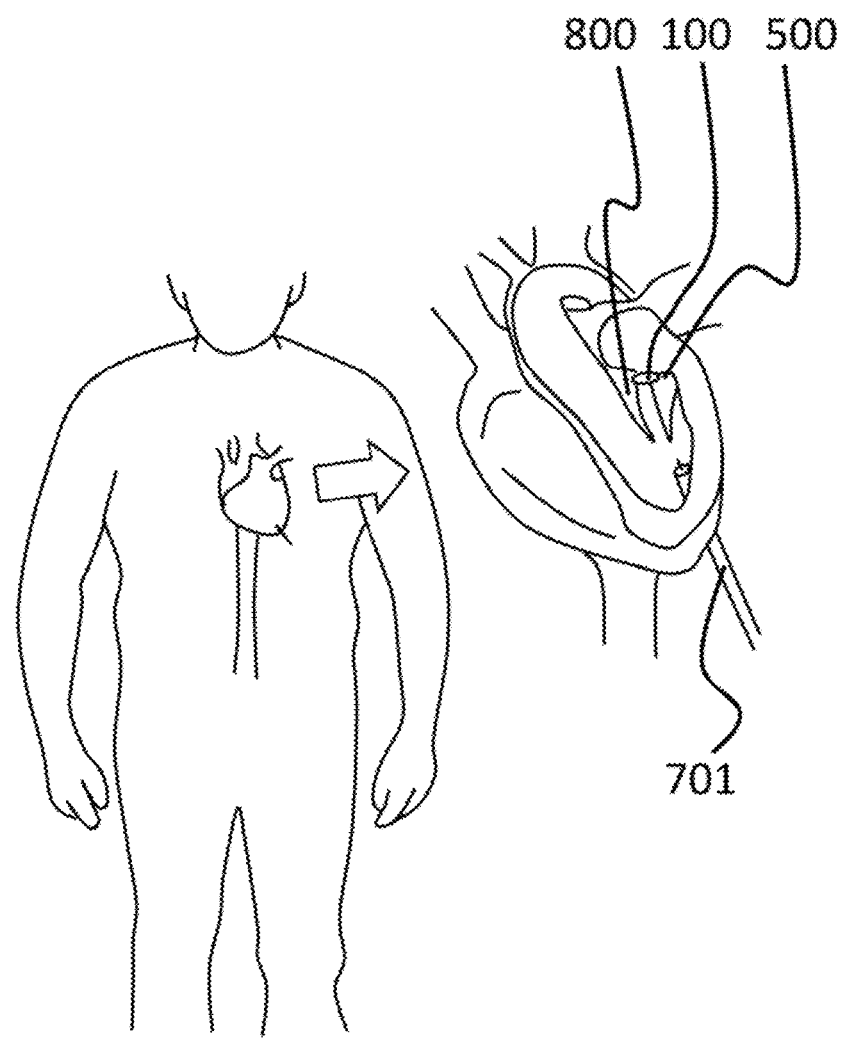
FIG. 8 is an illustration depicting an anatomical approach taken during a transapical mitral valve replacement according to the principles of the present invention.

For further illustration, FIG. 8 provides an illustration depicting the anatomical approach taken during a transapical mitral valve replacement according to the principles of the present invention. As shown, the catheter 701 is used for transapical implantation of the bioprosthetic mitral valve (of the present invention). Specifically, the cattier 701 is used to position the bioprosthetic mitral valve 100 in place against the patient's native mitral valve 800 and its corresponding native valve annulus 500 (as depicted in FIGS. 5B and 5C).

Thus, the mitral valve 100 according to the principles of the present invention is to be positioned into an existing human mitral valve 800 (i.e., the native mitral valve) and left in place to support the existing native mitral valve. In one aspect, the mitral valve 100 is simply left in place to support the existing, native mitral valve 800. In another non-limiting aspect, after being positioned into place, the mitral valve 100 can be further affixed with the existing native mitral valve 800 using any fixation technique. As a non-limiting example, the bioprosthetic mitral valve 100 can sewn or hooked against the native mitral valve 800. For example, the leaflets of the bioprosthetic mitral valve 100 can be sewn against the native mitral valve 800 leaflets. As another non-limiting example, the saddle-shaped frame of the bioprosthetic mitral valve 100 can be sewn against the native valve annulus 500. Such a process can be accomplished using any suitable mechanism or device that is operable fir in vivo fixation or stitching. As a non-limiting example, NeoChord, Inc. (located at 7700 Equitable Drive, Suite 206, Eden Prairie, Minn. 55344, USA) has developed a device for mitral valve repair that repairs, in vivo, torn leaflets with sutures. The Neochord mitral valve repair device can be employed to stitch the frame 102 against the native valve annulus 500 and/or the leaflets 106 against the native mitral valve leaflets. Thus, in this aspect, the Neochord device, instead of sewing a torn leaflet, is used to suture the mitral valve 100 in place against the native mitral valve 800.

Finally, it should be understood that the specific examples and dimensions as described and illustrated are provided as non-limiting examples of suitable aspects; however, the invention is not intended to be limited thereto as it can be modified as needed and is to be accorded the widest scope consistent with the principles and novel features disclosed herein.

What is claimed is:

1. A transcatheter mitral valve comprising:
 a wire annulus frame, having two prongs extending therefrom;
 two leaflets attached with the frame and prongs to form a bi-leaflet mitral valve;
 a fixture formed in the wire annulus frame to include one or more clamps; and
 wherein the wire annulus frame is a saddle-shaped annulus frame having an annulus rise reflecting curvature of the saddle-shaped annulus frame, the annulus rise having an apex, with the each of the one or more clamps being wire clamps projecting from the saddle-shaped annulus frame directly beneath the apex, whereby when the transcatheter mitral valve is implanted in a patient, a native mitral annulus is affixed between the apex and the one or more clamps.

2. The transcatheter mitral valve as set forth in claim 1, wherein the frame and prongs are formed of a shape memory material.

3. The transcatheter mitral valve as set forth in claim 2, wherein the shape memory material is Nitinol.

4. The transcatheter mitral valve as set forth in claim 3, wherein the saddle-shaped annulus frame is configurable between a collapsed configuration and an open configuration, such the collapsed configuration allows the transcatheter mitral valve to be delivered into position against a native mitral valve annulus and upon expanding to the open configuration, the transcatheter mitral valve is secured in place by the fixture.

5. The transcatheter mitral valve as set forth in claim 4, wherein the prongs have a prong length, the prong length being between 5 millimeters and 30 millimeters.

6. The transcatheter mitral valve as set forth in claim 5, wherein the prongs each include a prong axis and extend from the saddle-shaped annulus frame at an intersection, such that a prong angle exists between the prong axis and a vertical axis rising vertically from the intersection, where the prong angle is between 5 degrees and 40 degrees.

7. The transcatheter mitral valve as set forth in claim 6, wherein the leaflets are formed of a material selected from a group consisting of pericardial tissue, polymeric material, and leaflet tissue material.

8. The transcatheter mitral valve as set forth in claim 1, wherein the saddle-shaped annulus frame is configurable between a collapsed configuration and an open configuration, such the collapsed configuration allows the transcatheter mitral valve to be delivered into position against a native mitral valve annulus and upon expanding to the open configuration, the transcatheter mitral valve is secured in place by the fixture.

9. The transcatheter mitral valve as set forth in claim 1, wherein the leaflets are formed of a material selected from a group consisting of pericardial tissue, polymeric material, and leaflet tissue material.

10. The transcatheter mitral valve as set forth in claim 1, wherein the annulus rise is between 2 millimeters and 5 millimeters.

11. The transcatheter mitral valve as set forth in claim 1, wherein the prongs have a prong length, the prong length being between 5 millimeters and 30 millimeters.

12. The transcatheter mitral valve as set forth in claim 1, wherein the prongs each include a prong axis and extend from the frame at an intersection, such that a prong angle exists between the prong axis and a vertical axis rising vertically from the intersection, where the prong angle is between 5 degrees and 40 degrees.

13. The transcatheter mitral valve as set forth in claim 1, wherein the wire annulus frame is enclosed in fabric.

* * * * *